(12) United States Patent
Ebisawa

(10) Patent No.: US 11,643,389 B2
(45) Date of Patent: May 9, 2023

(54) METHOD FOR PRODUCING MALEIMIDE COMPOUND, COMPOUND AND SOLID RESIN

(71) Applicant: TOKYO OHKA KOGYO CO., LTD., Kawasaki (JP)

(72) Inventor: Kazuaki Ebisawa, Kawasaki (JP)

(73) Assignee: TOKYO OHKA KOGYO CO., LTD., Kawasaki (JP)

( * ) Notice: Subject to any disclaimer, the term of this patent is extended or adjusted under 35 U.S.C. 154(b) by 409 days.

(21) Appl. No.: 16/824,082

(22) Filed: Mar. 19, 2020

(65) Prior Publication Data

US 2020/0308112 A1 Oct. 1, 2020

(30) Foreign Application Priority Data

Mar. 28, 2019 (JP) .............................. JP2019-064748

(51) Int. Cl.
  *C07D 207/448* (2006.01)
  *C08F 212/08* (2006.01)
  *C07D 209/48* (2006.01)

(52) U.S. Cl.
  CPC ....... *C07D 207/448* (2013.01); *C07D 209/48* (2013.01); *C08F 212/08* (2013.01)

(58) Field of Classification Search
  None
  See application file for complete search history.

(56) References Cited

FOREIGN PATENT DOCUMENTS

| JP | 2014-169384 A | 9/2014 |
|----|---------------|--------|
| JP | 2017-048285 A | 3/2017 |
| KR | 10-1744925 B1 | 6/2017 |

OTHER PUBLICATIONS

Ke et al. "Synthesis, curing process and thermal reversible mechanism of UV curable polyurethane based on Diels-Alder structure" Progress in Organic Coatings, 2016, vol. 100, pp. 63-69.*

Kuroda et al. "Poly(p-maleimidostyrene) as a macromolecule initiator for polymerization of styrene-type monomers—Synthesis of block copolymers containing poly(p-maleimidostyrene) with highly reactive pendent maleimido groups". Polymer, vol. 51 Issue 13, pp. 2843-2848. Jun. 7, 2010.

* cited by examiner

*Primary Examiner* — Joseph R Kosack

(74) *Attorney, Agent, or Firm* — Knobbe, Martens, Olson & Bear LLP

(57) ABSTRACT

A method for producing a maleimide compound having a group represented by the formula (a1), the method including condensing a primary amino group in a raw material compound having the primary amino group and dicarboxylic anhydride represented by the formula (a2) to generate a group represented by the formula (a3); and heating a compound having the group represented by the formula (a3), and converting the group represented by the formula (a3) into the group represented by the formula (a1).

8 Claims, 2 Drawing Sheets

METHOD FOR PRODUCING MALEIMIDE COMPOUND, COMPOUND AND SOLID RESIN

This application claims priority to Japanese Patent Application No. 2019-064748, filed Mar. 28, 2019, the entire content of which is incorporated herein by reference.

BACKGROUND OF THE INVENTION

Field of the Invention

The present invention relates to a method for producing a maleimide compound, a compound, and a solid resin.

Related Art

It is known to impart desired properties to various compounds by introducing various functional groups into various low molecular weight compounds and high molecular weight compounds. For example, introduction of a maleimide group into a compound is often performed. Introduction of the maleimide group imparts radical polymerizability to a compound. For example, when a resin in which a maleimide group has been introduce is obtained, a method of polymerizing a monomer including a compound having a maleimide group is considered (see, for example, Non-Patent Document 1). However, in this method, the polymerization form when a monomer including a compound having a maleimide group is polymerized is limited to cationic polymerization. Therefore, this method time-consuming, and synthesis cannot be performed in a simple and easy manner. Furthermore, since the polymerization uses a metal catalyst, when the obtained maleimide group-containing resin is used in an application in which a presence of a metal is not desired, there is a problem that the maleimide group-containing resin needs to be highly purified. Furthermore, examples of a method for introducing a maleimide group into a styrene resin include a method of reacting maleic anhydride with a styrene resin having a primary amino group to close a ring. However, this method causes a problem that gelation may occur and a solid resin cannot be obtained, and a problem that a maleimide group is not easily formed by a ring closure reaction. This seems to be because the above-mentioned introduction method of a maleimide group easily cause a side reaction other than desired maleimidization. Therefore, there has been a demand for a production method capable of obtaining a resin having a maleimide group without using a metal catalyst for a short time in a simple and easy manner while a side reaction other than maleimidization is suppressed. Note here that when a maleimide group is introduced into not only a styrene resin having an amino group, but also a various other compounds having an amino group, there has been, similarly, a demand for a production method capable of obtaining a maleimide compound in a simple and easy manner while a side reaction other than maleimidization is suppressed.

Non-Patent Document 1: Shigeo Kuroda; Tokio Hagiwara, Polymer Volume 51, Issue 13 Pages 2843-2848

SUMMARY OF THE INVENTION

The present invention has been made in view of the above-mentioned problems. An object of the present invention is to provide a method for producing a maleimide compound, capable of obtaining a maleimide compound in a simple and easy manner while a side reaction other than maleimidization is suppressed; a compound; and a method for producing a solid resin.

The present inventors have found that a maleimide compound can be obtained in a simple and easy manner by a production method including condensing a primary amino group in a raw material compound having the primary amino group and a dicarboxylic anhydride represented by the following formula (a2) to generate a group represented by the following formula (a3), heating a compound having the generated group represented by the formula (a3) and converting the group represented by the formula (a3) into a group represented by the formula (a1), while a side reaction other than maleimidization is suppressed, and have completed the present invention.

A first aspect of the present invention is a method for producing a maleimide compound having a group represented by the following formula (a1):

[Chem. 1]

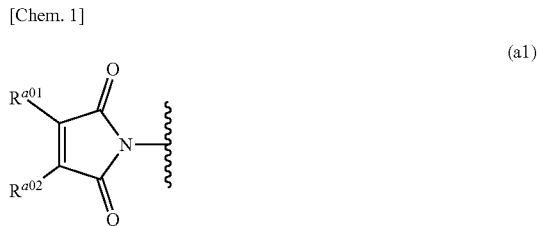

(a1)

(wherein, in the formula (a1), $R^{a01}$ and $R^{a02}$ are each independently a hydrogen atom, an alkyl group having 1 or more and 6 or less carbon atoms, a cycloalkyl group having 3 or more and 8 or less carbon atoms, or an aryl group having 6 or more and 12 or less carbon atoms), the method including: a first step of condensing a primary amino group in a raw material compound having the primary amino group and dicarboxylic anhydride represented by the following formula (a2):

[Chem. 2]

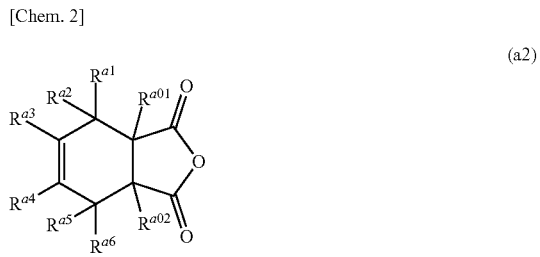

(a2)

(wherein, in the formula (a2), $R^{a01}$ and $R^{a02}$ are the same as $R^{a01}$ and $R^{a02}$ in the formula (a1), $R^{a1}$ to $R^{a6}$ are each independently a hydrogen atom, a halogen atom, an alkyl group having 1 or more and 4 or less carbon atoms, or an alkoxy group having 1 or more and 4 or less carbon atoms, $R^{a1}$ and $R^{a5}$ may be bonded to each other to form —O—, —S—, —CH$_2$—, or —CR$^{a7}$R$^{a8}$—, and $R^{a3}$ and $R^{a4}$ may be bonded to each other to form a ring having 6 or more and 12 or less carbon atoms, $R^{a7}$ to $R^{a8}$ are each independently a hydrogen atom, an alkyl group having 1 or more and 4 or less carbon atoms or an alkoxy group having 1 or more and 4 or less carbon atoms) to generate a group represented by the following formula (a3):

[Chem. 3]

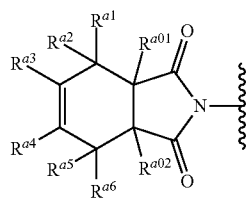

(a3)

(wherein, in the formula (a3), $R^{a01}$ and $R^{a02}$ are the same as Ran and $R^{a02}$ in the formula (a1), and $R^{a1}$ to $R^{a6}$ are the same as $R^{a1}$ to $R^{a6}$ in the formula (a2)); and a second step of heating a compound having the group represented by the formula (a3) generated in the first step, and converting the group represented by the formula (a3) into a group represented by the formula (a1).

A second aspect of the present invention is a compound having a group represented by the following formula (a3):

[Chem. 4]

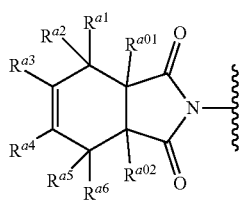

(a3)

(wherein in the formula (a3), $R^{a01}$ and $R^{a02}$ are each independently a hydrogen atom, an alkyl group having 1 or more and 6 or less carbon atoms, a cycloalkyl group having 3 or more and 8 or less carbon atoms, or an aryl group having 6 or more and 12 or less carbon atoms, $R^{a1}$ to $R^{a6}$ are each independently a hydrogen atom, a halogen atom, an alkyl group having 1 or more and 4 or less carbon atoms, or an alkoxy group having 1 or more and 4 or less carbon atoms, $R^{a1}$ and $R^{a5}$ may be bonded to each other to form —O—, —S—, —CH$_2$—, or —CR$^{a7}$R$^{a8}$—, and $R^{a3}$ and $R^{a4}$ may be bonded to each other to form a ring having 6 or more and 12 or less carbon atoms, $R^{a7}$ to $R^{a8}$ are each independently a hydrogen atom, an alkyl group having 1 or more and 4 or less carbon atoms or an alkoxy group having 1 or more and 4 or less carbon atoms).

A third aspect of the present invention is a resin in a form of a solid including a group represented by the following formula (a1) at a terminal of the side chain:

[Chem. 5]

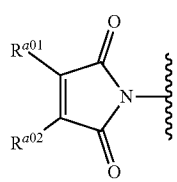

(a1)

(in the formula (a1), $R^{a01}$ and $R^{a02}$ are each independently a hydrogen atom, an alkyl group having 1 or more and 6 or less carbon atoms, a cycloalkyl group having 3 or more and 8 or less carbon atoms, or an aryl group having 6 or more and 12 or less carbon atoms), and being a polymer of a monomer having an unsaturated double bond.

The present invention can provide a method for producing a maleimide compound, capable of producing a maleimide compound in a simple and easy manner while a side reaction is suppressed; a compound; and a method for producing a solid resin.

DETAILED DESCRIPTION OF THE INVENTION

Figure 1:
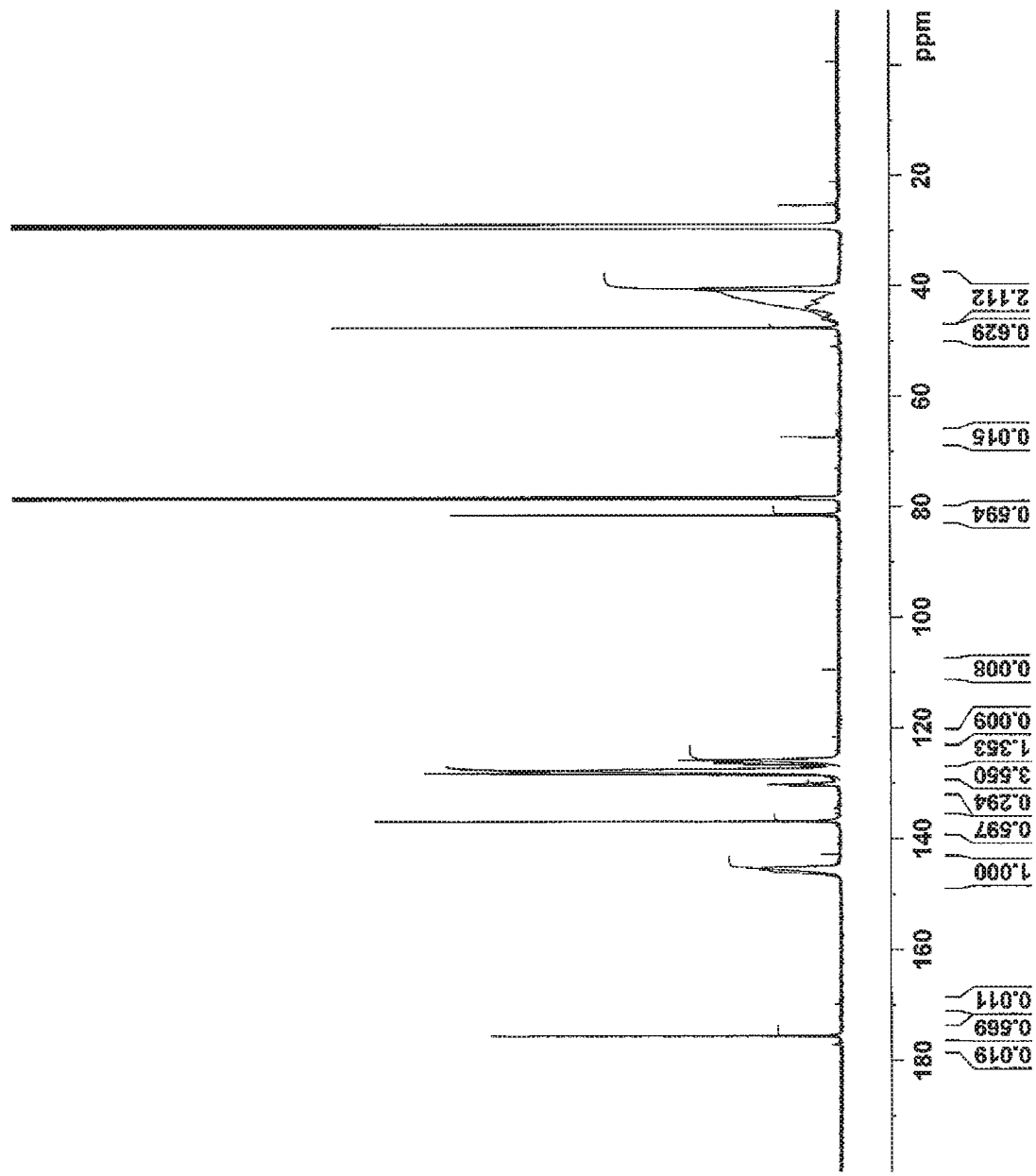
FIG. 1 is a view showing $^{13}$C NMR measurement result of a protected resin 1.

A method for producing a maleimide compound is a method for producing a maleimide compound having a group represented by the following formula (a1):

[Chem. 6]

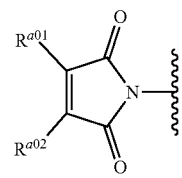

(a1)

(wherein, in the formula (a1), $R^{a01}$ and $R^{a02}$ are each independently a hydrogen atom, an alkyl group having 1 or more and 6 or less carbon atoms, a cycloalkyl group having 3 or more and 8 or less carbon atoms, or an aryl group having 6 or more and 12 or less carbon atoms).

Note here that in the specification and claims of the present application, a substituted or non-substituted cyclic imide group represented by the formula (a1) is referred to as a "maleimide group" for convenience sake. Furthermore, a compound having the maleimide group represented by the formula (a1) is referred to as a "maleimide compound."

The method for producing a maleimide compound mentioned above includes: a first step of condensing a primary amino group in a raw material compound having the primary amino group and dicarboxylic anhydride represented by the following formula (a2):

[Chem. 7]

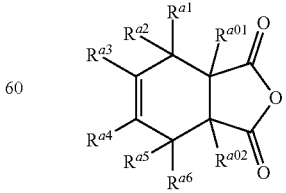

(a2)

(wherein, in the formula (a2), $R^{a01}$ and $R^{a02}$ are the same as $R^{a01}$ and $R^{a02}$ in the formula (a1), $R^{a1}$ to $R^{a6}$ are each independently a hydrogen atom, a halogen atom, an alkyl group having 1 or more and 4 or less carbon atoms, or an alkoxy group having 1 or more and 4 or less carbon atoms, $R^{a1}$ to $R^{a6}$ may be bonded to each other to form —O—, —S—, —CH$_2$—, or —CR$^{a7}$R$^{a8}$—, and R$^{a3}$ and R$^{a4}$ may be bonded to each other to form a ring having 6 or more and 12 or less carbon atoms, $R^{a7}$ to $R^{a8}$ are each independently a hydrogen atom, an alkyl group having 1 or more and 4 or less carbon atoms or an alkoxy group having 1 or more and 4 or less carbon atoms)
to generate a group represented by the following formula (a3):

[Chem. 8]

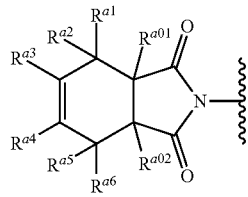

(a3)

(wherein in the formula (a3), $R^{a01}$ and $R^{a02}$ are the same as $R^{a01}$ and $R^{a02}$ in the formula (a1), and $R^{a1}$ to $R^{a6}$ are the same as $R^{a1}$ to $R^{a6}$ in the formula (a2));
and a second step of heating a compound having the group represented by the formula (a3) generated in the first step, and converting the group represented by the formula (a3) into a group represented by the formula (a1).

The alkyl group having 1 or more and 6 or less carbon atoms as $R^{a01}$ and $R^{a02}$ in the formula (a1) may be linear or branched, and specific examples thereof include a methyl group, an ethyl group, an n-propyl group, an n-butyl group, an n-pentyl group, an n-hexyl group, an isopropyl group, an isobutyl group, a sec-butyl group, a tert-butyl group, an isopentyl group, a neopentyl group, a tert-pentyl group, an isohexyl group. Specific examples of the cycloalkyl group having 3 or more and 8 or less carbon atoms as $R^{a01}$ and $R^{a02}$ in the formula (a1) include a cyclopropyl group, a cyclobutyl group, a cyclopentyl group, and a cyclohexyl group. Specific examples of the aryl group having 6 or more and 12 or less carbon atoms as $R^{a01}$ and $R^{a02}$ in the formula (a1) include a phenyl group, a biphenyl group, a 1-naphthyl group, and a 2-naphthyl group. It is preferable that both $R^{a01}$ and $R^{a02}$ in the formula (a1) are a hydrogen atom. When both of the $R^{a01}$ and $R^{a02}$ are a hydrogen atom, since homo-photopolymerizability is high, a maleimide compound having a group represented by the formula (a1) is suitable for a photosensitive resin for example. When both of the $R^{a01}$ and $R^{a02}$ are a hydrogen atom, a group represented by the formula (a1) is a non-substituted maleimide group.

Specific examples of a halogen atom as $R^{a1}$ to $R^{a6}$ in the formula (a2) include a chlorine atom, a fluorine atom, a bromine atom, and an iodine atom. The alkyl group having 1 or more and 4 or less carbon atoms as $R^{a1}$ to $R^{a6}$ in the formula (a2) may be a linear or branched chain, and specific examples thereof include a methyl group, an ethyl group, an n-propyl group, an n-butyl group, an isopropyl group, an isobutyl group, an sec-butyl group, and a tert-butyl group. The alkoxy group having 1 or more and 4 or less carbon atoms as $R^{a1}$ to $R^{a6}$ in the formula (a2) may be a linear or branched chain, and specific examples thereof include a methoxy group, an ethoxy group, an n-propoxy group, an isopropoxy group, and an n-butoxy group. The alkyl group having 1 or more and 4 or less carbon atoms as $R^{a7}$ to $R^{a8}$ and an alkoxy group having 1 or more and 4 or less carbon atoms are the same as the alkyl group having 1 or more and 4 or less carbon atoms and the alkoxy group having 1 or more and 4 or less carbon atoms as $R^{a1}$ to $R^{a6}$.

In the first step, a primary amino group in the raw material compound having the primary amino group, and a dicarboxylic anhydride represented by the above formula (a2) are condensed to each other to generate a group represented by the above formula (a3). Thus, a compound having the group represented by the formula (a3) is obtained.

The raw material compound having a primary amino group is not particularly limited, and may be a resin or a compound other than a resin. In the present specification, the "resin" means a compound having a mass average molecular weight (Mw) of 4000 or more. The mass average molecular weight (Mw) of the resin is more preferably 5000 or more, and further preferably 10000 or more. The molecular weight of the resin (A) is preferably 100000 or less, and more preferably 80000 or less as the mass average molecular weight (Mw). In this specification, the mass average molecular weight (Mw) is a measurement value based on polystyrene by gel permeation chromatography (GPC).

As the resin as a raw material compound having a primary amino group, a polymer of a monomer having an unsaturated double bond is exemplified. Examples of such resins include a (meth)acrylic resin having a primary amino group, and a polystyrene resin having a primary amino group. More specific examples thereof include a (meth)acrylic resin having a primary amino group at a terminal of a side chain, and a polystyrene resin having a primary amino group at the terminal of the side chain. Note here that in this specification, "(meth)acrylic" means both "acrylic" and "methacrylic". The "(meth)acrylic resin" is a resin including a constituent unit derived from one or more monomer selected from the group consisting of (meth)acrylic acid, (meth)acrylic ester, and optionally N-substituted (meth)acrylamide. The (meth)acrylic resin may include a constituent unit derived from a monomer other than (meth)acrylic acid, (meth)acrylic ester, and optionally N-substituted (meth)acrylamide. The "(meth)acrylic resin having a primary amino group" is a (meth)acrylic resin including a constituent unit having a primary amino group. The constituent unit having a primary amino group may be a constituent unit derived from (meth)acrylic ester, or a constituent unit derived from an N-substituted body of (meth)acrylamide, or constituent units other than these constituent units. The constituent unit having a primary amino group is preferably a constituent unit derived from (meth)acrylic ester, and/or a constituent unit derived from the N-substituted body of (meth)acrylamide. The "polystyrene resin" means a resin including a constituent unit derived from styrene and/or styrene derivative. The "polystyrene resin having a primary amino group" is a polystyrene resin including a constituent unit having a primary amino group. The constituent unit having a primary amino group may be a constituent unit derived from amino styrene such as p-amino styrene, m-amino styrene, and o-amino styrene, or a constituent unit derived from styrene derivatives having an amino group such as p-aminomethylstyrene, m-aminomethylstyrene, and o-aminomethylstyrene, or constituent units other than these constituent units. The constituent unit having a primary amino group is preferably a constituent unit derived from amino styrene, and/or a constituent unit derived from styrene derivative having an amino group. Resins including the primary amino group, such as a (meth)acrylic resin having a primary amino group and a polystyrene resin having a primary amino group preferably include a primary amino group at the terminal of the side chain. In the (meth)acrylic resin having a primary amino group at the terminal of the side chain, and the polystyrene resin having a primary amino group at the terminal of the side chain, the terminal of the side chain to which a primary amino group when the side chain is a branched chain is bonded may be any terminals of two or more of the branched chains. Furthermore, when a structure of the terminals of the side chain has a ring structure, an arbitrary position of the ring constituting the ring structure is a terminal of the side chain to which the primary amino group is bonded. For example, when the side chain includes an α-naphthyl group or β-naphthyl group, the arbitrary position on the naphthalene ring is a terminal of the side chain. Furthermore, when the group constituting the side chain is a 1-phenyl ethyl group that is a branched chain, the terminal of the side chain is a methyl group corresponding to the terminals of the two branched chains and arbitrary position on the phenyl group.

Note here that in the specification of the present application, a resin including a constituent unit derived from one or more monomers selected from the group consisting of (meth)acrylic acid, (meth)acrylic ester, and optionally N-substituted (meth)acrylamide, and a constituent unit derived from styrene and/or styrene derivative are handled as a (meth)acrylic resin for convenience sake.

When a resin having a primary amino group is used as a raw material compound, the above-mentioned method for producing a maleimide compound preferably includes producing a raw material compound being a resin by homopolymerizing a monomer having a primary amino group; or producing a raw material compound being a resin by copolymerizing a monomer having a primary amino group and a comonomer. Examples of the monomer having a primary amino group include (meth)acrylates such as aminomethyl (meth)acrylate, 2-aminoethyl (meth) acrylate, 3-aminopropyl (meth) acrylate, 4-aminophenyl (meth) acrylate, 3-aminophenyl (meth) acrylate, 2-aminophenyl (meth) acrylate, 4-aminophenylmethyl (meth) acrylate, 3-aminophenylmethyl (meth) acrylate, and 2-aminophenylmethyl (meth) acrylate; (meth)acrylamides such as N-2-aminoethyl (meth) acrylamide, N-3-aminopropyl (meth)acrylamide, N-4-aminophenyl (meth)acrylamide, N-3-aminophenyl (meth) acrylamide, and N-2-aminophenyl (meth)acrylamide; amino styrene such as p-amino styrene, m-amino styrene, and o-amino styrene; aminoalkylstyrene such as p-aminomethylstyrene, m-aminomethylstyrene, and o-aminomethylstyrene, and the like.

The comonomer is a monomer other than the monomer having a primary amino group. Examples of the comonomer include a compound represented by the following formula (a-I).

(a-I)

In the formula (a-I), $R^{a10}$ is a monovalent organic group, and $R^{a11}$ is a hydrogen atom or a methyl group. This organic group may include a bond or a substituent other than a hydrocarbon group such as a hetero atom in the organic group, and the like. Furthermore, this organic group may be linear or branched or cyclic.

The substituent other than the hydrocarbon group in the organic group of $R^{a10}$ is not particularly limited as long as the present invention are not impaired, and examples thereof include a halogen atom, a hydroxyl group, a mercapto group, a sulfide group, a cyano group, an isocyano group, a cyanato group, an isocyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxy group, a carboxylate group, an acyl group, an acyloxy group, a sulfino group, a sulfo group, a sulfonato group, a phosphino group, a phosphinyl group, a phosphono group, a phosphonato group, a hydroxy imino group, an alkyl ether group, an alkylthioether group, an arylether group, an arylthioether group, an N-monosubstituted amino group, an N,N-disubstituted amino group, and the like. The hydrogen atom included in the above-mentioned substituents may be substituted with a hydrocarbon group. Furthermore, a hydrocarbon group included in the above-mentioned substituent may be any of linear, branched, and cyclic.

As $R^{a10}$, an alkyl group, an aryl group, an aralkyl group, or a heterocyclic group is preferable. These groups may be substituted with a halogen atom, a hydroxyl group, an alkyl group, or a heterocyclic group. Furthermore, when these groups include an alkylene moiety, the alkylene moiety may be interrupted by an ether bond, a thioether bond, or an ester bond.

When the alkyl group is linear or branched, the number of carbon atoms is preferably 1 or more and 20 or less, more preferably 1 or more and 15 or less, and particularly preferably 1 or more and 10 or less. Suitable examples of the alkyl group include a methyl group, an ethyl group, an n-propyl group, an isopropyl group, an n-butyl group, an isobutyl group, an sec-butyl group, a tert-butyl group, an n-pentyl group, an isopentyl group, an sec-pentyl group, a tert-pentyl group, an n-hexyl group, an n-heptyl group, an n-octyl group, an isooctyl group, an sec-octyl group, a tert-octyl group, an n-nonyl group, an isononyl group, an n-decyl group, an isodecyl group, and the like.

When the alkyl group is an alicyclic group, or a group including an alicyclic group, examples of the suitable alicyclic group included in the alkyl group include monocyclic alicyclic groups such as a cyclopentyl group and a cyclohexyl group, polycyclic alicyclic groups such as an adamantyl group, a norbornyl group, an isobornyl group, a tricyclononyl group, a tricyclodecyl group, and a tetracyclo dodecyl group.

The other preferable examples of the comonomer include (meth)acrylamide, unsaturated carboxylic acid, an allyl compound, vinyl ether, vinyl ester, styrene, and the like. These comonomers can be used singly or in combination of two or more.

Examples of (meth)acrylamides include (meth)acrylamide; N-alkyl(meth)acrylamide such as N-methyl(meth)acrylamide, N-ethyl(meth)acrylamide, N-n-propyl(meth)acrylamide, N-isopropyl(meth)acrylamide, and N-n-butyl(meth) acrylamide; N-aryl(meth)acrylamide such as N-phenyl (meth)acrylamide, N-α-naphthyl(meth)acrylamide, and N-β-naphthyl(meth)acrylamide; N,N-dialkyl(meth)acrylamide such as N,N-dimethyl(meth)acrylamide, N,N-diethyl (meth)acrylamide, N,N-di-n-propyl(meth)acrylamide, and N,N-di-n-butyl(meth)acrylamide; N,N-diaryl(meth)acrylamide such as N,N-diphenyl(meth)acrylamide; and other N,N disubstituted (meth)acrylamide such as N-methyl-N-phenyl(meth)acrylamide, and N-hydroxyethyl-N-methyl (meth)acrylamide.

Examples of unsaturated carboxylic acid include monocarboxylic acid such as crotonic acid; dicarboxylic acid such as maleic acid, fumaric acid, citraconic acid, mesaconic acid, and itaconic acid; anhydride of these dicarboxylic acid, and the like.

Examples of the allyl compound include allyl esters such as allyl acetate, allyl caproate, allyl caprylate, allyl laurate, allyl palmitate, allyl stearate, allyl benzoate, allyl acetoacetate and allyl lactate; and allyloxyethanol, and the like.

Examples of the vinyl ethers include an alkyl vinyl ether such as hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether or tetrahydrofurfuryl vinyl ether; and a vinyl aryl ether such as vinyl phenyl ether, vinyl tolyl ether, vinyl chlorophenyl ether, vinyl-2,4-dichlorophenyl ether, vinyl naphthyl ether or vinyl anthranyl ether.

Examples of the vinyl esters include vinyl butyrate, vinyl isobutyrate, vinyl trimethyl acetate, vinyl diethyl acetate, vinyl valate, vinyl caproate, vinyl chloroacetate, vinyl dichloroacetate, vinyl methoxyacetate, vinyl butoxyacetate, vinyl phenyl acetate, vinyl acetoacetate, vinyl lactate, vinyl-β-phenyl butyrate, vinyl benzoate, vinyl salicylate, vinyl chlorobenzoate, vinyl tetrachlorobenzoate and vinyl naphthoate.

Examples of the styrenes include styrene; alkyl styrene such as methylstyrene, dimethylstyrene, trimethylstyrene, ethylstyrene, diethylstyrene, ispropylstyrene, butylstyrene, hexylstyrene, cyclohexylstyrene, decylstyrene, benzylstyrene, chloromethylstyrene, trifluoromethylstyrene, ethoxymethylstyrene or acetoxymethylstyrene; alkoxystyrene such as methoxystyrene, 4-methoxy-3-methylstyrene or dimethoxystyrene; and halostyrene such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene or 4-fluoro-3-trifluoromethylstyrene.

When the monomer having a primary amino group and the comonomer are copolymerized, the ratio of the monomer having a primary amino group to the comonomer is not particularly limited, but the ratio of the monomer having a primary amino group:comonomer is, for example, 5 to 50:50 to 95 on a molar basis.

Examples of the a raw material compound having a primary amino group other than a resin include aliphatic amine such as ethylamine, n-propylamine, isopropylamine, n-butylamine, n-pentylamine, n-hexylamine, n-octylamine, ethylenediamine, 1,2-propane diamine, 1,3-propane diamine, 1,4-butane diamine, hexamethylene diamine, diethylene triamine, triethylene tetramine, and hexamethylene tetramine; aromatic amine such as aniline, 4-methylaniline, 3-methylaniline, 2-methylaniline, 4-chloroaniline, 3-chloroaniline, 2-chloroaniline, p-aminostyrene, m-aminostyrene, o-aminostyrene, p-aminomethylstyrene, m-aminomethylstyrene, o-aminomethylstyrene, p-phenylenediamine, m-phenylenediamine, o-phenylenediamine, 2,4-diaminotoluene, 3,3'-diaminobiphenyl, 4,4'-diaminobiphenyl, 2,2'-diaminobiphenyl, 4,3'-diaminobiphenyl, 4,4'-diamino-2,2'-bis(trifluoromethyl) biphenyl, 3,3'-diaminodiphenyl ether, 3,4'-diaminodiphenyl ether, 4,4'-diaminodiphenyl ether, 3,3'-diaminodiphenylsulfone, 3,4'-diaminodiphenylsulfone, 4,4'-diaminodiphenylsulfone, 3,3'-diaminodiphenyl methane, 3,4'-diaminodiphenyl methane, 4,4'-diaminodiphenyl methane, 4,4'-diaminodiphenyl sulfide, 3,3'-diaminndiphenylketone, 3,4'-diaminndiphenylketone, 2,2-bis(p-aminophenyl)propane, 2,2'-bis(p-aminophenyl)hexafluoropropane, 4-methyl-2,4-bis(p-aminophenyl)-1-pentene, 4-methyl-2,4-bis(p-aminophenyl)-2-pentene, iminodianiline, 4-methyl-2,4-bis(p-aminophenyl)pentane, bis(p-aminophenyl)phosphine oxide, 4,4'-diaminoazobenzene, 4,4'-diaminodiphenylurea, 4,4'-diaminodiphenylamide, 1,4-bis(4-aminophenoxy)benzene, 1,3-bis(4-aminophenoxy)benzene, 1,3-bis(3-aminophenoxy)benzene, 4,4'-bis(4-aminophenoxy)biphenyl, bis[4-(4-aminophenoxy)phenyl]sulfone, bis[4-(3-aminophenoxy)phenyl]sulfone, 2,2-bis[4-(4-aminophenoxy)phenyl] propane, 2,2-bis[4-(4-aminophenoxy)phenyl] hexafluoropropane, 1,3-bis(m-aminophenoxy)benzene, 1,3-bis(p-aminophenoxy)benzene, 1,4-bis(p-aminophenoxy) benzene, 1,5-diaminonaphthalene, and 2,6-diaminonaphthalene.

The compound represented by the formula (a2) includes a compound represented by the following formula (a2-1):

[Chem. 9]

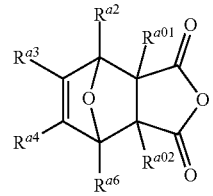

(a2-1)

(wherein, in the formula (a2-1), $R^{a01}$, $R^{a02}$, $R^{a2}$, $R^{a3}$, $R^{a4}$, and $R^{a6}$ are the same as $R^{a01}$, $R^{a02}$, $R^{a2}$, $R^{a3}$, $R^{a4}$, and $R^{a6}$ in the formula (a2)).

The compound represented by the formula (a2) can be obtained by, for example, a Diels-Alder reaction between the compound represented by the following formula and a conjugate diene compound corresponding to the structure of the compound represented by the formula (a2). Conditions for the Diels-Alder reaction may be appropriately set according to types of raw materials to be used, and reaction in an organic solvent may be performed.

[Chem. 10]

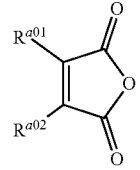

Examples of the organic solvent to be used in the Diels-Alder reaction include esters such as ethyl acetate, butyl acetate, and cellosolve acetate; ketones such as acetone, methyl ethyl ketone, isobutyl ketone, and methyl isobutyl ketone; esters such as ethyl acetate, butyl acetate, and diethyl malonate; amides such as N-methyl-pyrrolidone, and N,N-dimethylformamide; ethers such as diethyl ether, ethyl cyclopentyl ether, tetrahydrofuran, and dioxane; aromatic hydrocarbons such as toluene, and xylene; aliphatic hydrocarbons such as hexane, heptane, octane, and decahydronaphthalene, and halogenated hydrocarbons such as methylene chloride, and ethylene chloride; dimethyl sulfoxide, dimethyl sulfonamide, and the like. As the organic solvent to be used, one kind of solvent may be used, or an arbitrary combination of two more kinds of solvents may be used. The reaction temperature that can be employed is, for example, in a range of −10° C. to 200° C., preferably in a range of 0° C. to 150° C., and more in a range of 5° C. to 120° C. The reaction time that can be employed is, for example, 5 minutes or more and 12 hours or less, 10 minutes or more and 10 hours, and 30 minutes or more and 8 hours or less.

The condensation in the first step is usually performed using a condensing agent. Examples of the dehydration-condensation agent include carbonyl diimidazole, a carbodiimide compound, and the like. The addition of a condensing agent may be performed to a reactor vessel in which the Diels-Alder reaction was performed, or may be performed by separately isolating the product in the Diels-Alder reaction and dissolving it in an organic solvent or the like, again. As the organic solvents to be used in the condensation, the same organic solvents to be used for the Diels-Alder reaction can be employed. The reaction temperature that can be employed is, for example, in a range of −10° C. to 200° C., preferably in a range of 0° C. to 150° C., and more in a range of 5° C. to 120° C. The reaction time that can be employed is, for example, 5 minutes or more and 12 hours or less, 10 minutes or more and 10 hours or less, and 30 minutes or more and 8 hours or less.

Note here that a compound having a group represented by the above formula (a3) obtained by carrying out the first step may be isolated after the first step. When the compound having the group represented by the above formula (a3) is a resin, the isolation is performed, for example, by pouring a reaction solution after condensation in the first step into a poor solvent to solidify thereof, and collecting by filtering thereof.

In the second step, the compound having the group represented by the above formula (a3), generated in the first step, is heated to convert the group represented by the above formula (a3) into the group represented by the above formula (a1) (reverse Diels-Alder reaction). Thus, a maleimide compound having the group represented by the above formula (a1) is obtained. The group represented by the above formula (a1) can be introduced into all or a part of the amino group derived from the monomer having a primary amino group as the raw material compound depending on the use amount of the compound represented by the formula (a2).

The reverse Diels-Alder reaction in the second step is performed in, for example, an organic solvent. As the organic solvent to be used, the same organic solvent as that used in the Diels-Alder reaction can be employed, but for performing a reaction by heating, the solvent has a boiling point of preferably 60° C. or more, more preferably 80° C. or more, and further preferably 100° C. or more. The upper limit of the boiling point is not particularly limited, but it is, for example, 350° C. or less. As to the heating in the second step, the reaction temperature that can be employed is, for example, in a range of 60° C. to 280° C., preferably in a range of 80° C. to 250° C., and more preferably in a range of 100° C. to 225° C. The reaction time that can be employed is, for example, 5 minutes or more and 12 hours or less, preferably 10 minutes or more and 10 hours or less, and more preferably 30 minutes or more and 8 hours or less.

Furthermore, a compound having a group represented by the above formula (a1) obtained by carrying out the second step may be isolated after the second step. When the compound having the group represented by the above formula (a1) is a resin, the isolation is performed, for example, by pouring a reaction solution after condensation in the second step into a poor solvent (for example, alcohol solvent) to solidify thereof, and collecting by filtering thereof.

As one example of the method for producing a maleimide compound, a reaction formula in a case where a product obtained by copolymerizing amino styrene as the monomer having a primary amino group and styrene as a comonomer is used as a raw material compound having a primary amino group. In the following reaction formula, the second step shows an example in which reflux is performed in toluene. Furthermore, m and n in the following reaction formula each represent the number of repetition of constituent units.

[Chem. 11]

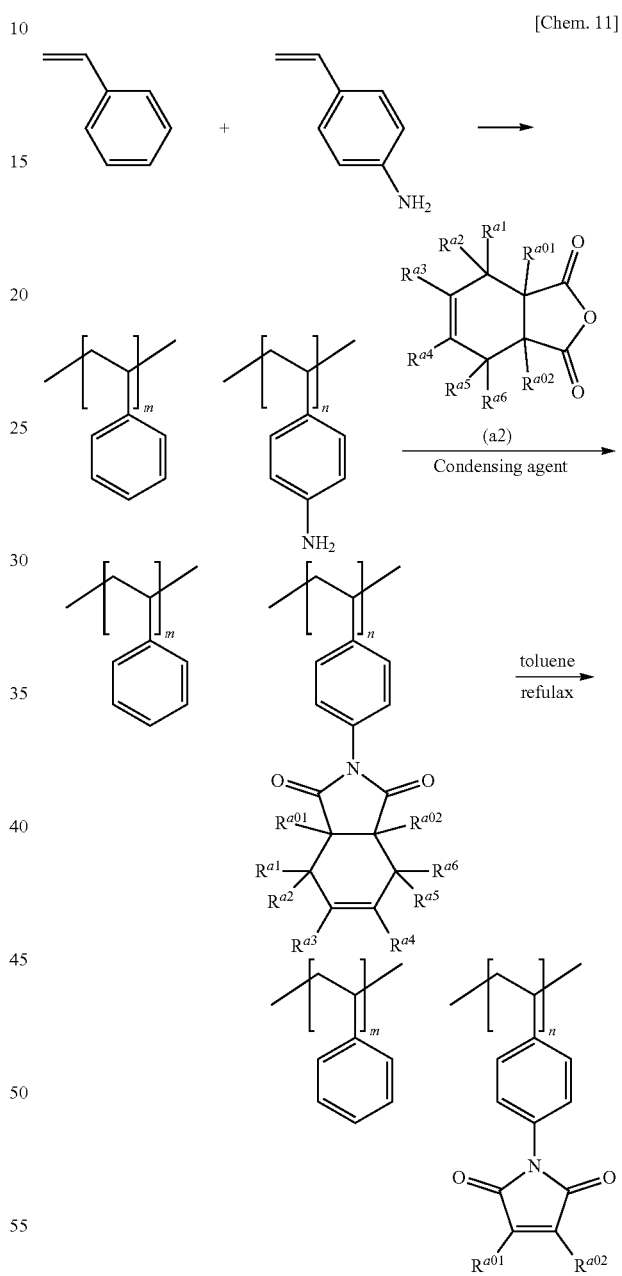

According to such a production method of the present invention, a side reaction other than maleimidization is suppressed. As a result of suppression of the side reaction, when the raw material compound is a resin having a primary amino group, a maleimide compound having a group represented by the formula (a1) can be obtained as a solid resin. Herein, "a resin in a form of a solid" is also referred to as "a solid resin". Therefore, for example, in various compositions, the maleimide compound having a group represented by the formula (a1) as a solid resin can be blended. For example, since a polymer of a monomer having an unsaturated double bond including the group represented by the above formula (a1) at the terminal of the side chain had a problem of gelation mentioned above, conventionally it was not able to be obtained as the solid resin. According to the above-mentioned production method, however, a polymer of a monomer having an unsaturated double bond, including the group represented by the formula (a1), is obtained as a solid resin. Note here that also in a case where the maleimide compound having a group represented by the formula (a1) is a compound that is not a resin, similarly, it can be obtained as a solid compound.

Furthermore, according to the above-mentioned production method, when the maleimide compound having a group represented by the formula (a1) is a resin, a polymer that has been polymerized in advance is used as a raw material compound and a primary amino group of a polymer is reacted to introduce a group represented by the formula (a1). Therefore, the polymerization is not limited to time-consuming cationic polymerization. Therefore, the production method of the present invention is a simple and easy method.

Furthermore, after the primary amino group and the dicarboxylic anhydride represented by the formula (a2) are condensed to each other to generate a group represented by the formula (a3), the obtained product is heated to convert a group represented by the formula (a3) into a group represented by the formula (a1). Therefore, problems by ring closure reaction do not occur. Thus, a group represented by the formula (a1) can be introduced reliably.

Note here that the compound having the group represented by the formula (a3) generated in the first step is a new compound.

EXAMPLES

Hereinafter, the present invention is described in more detail by way of Examples, but the present invention is not limited to these Examples.
<Preparation of Raw Material Compound Having Primary Amino Group>
[Preparation of P1 Precursor]

In a three-neck flask, propylene glycol monomethyl ether acetate (PGMEA) (242 g) was added, and the obtained product was heated to 80° C. under a nitrogen atmosphere. Styrene (85 g), 4-amino styrene (97 g), and an azo polymerization initiator (product name: V-601, manufactured by FUJIFILM Wako Pure Chemical Corporation) (29 g) were dissolved in PGMEA (242 g), and the obtained product was dropped into the three-neck flask over four hours. After completion of dropping, the obtained product was stirred at 80° C. for two hours, and the obtained polymeric solution was dropped to a methanol-water mixed solution (methanol/water=4/1 (on a mass basis)) (2.5 kg) and allowed to reprecipitate to obtain 72.8 g of copolymer (P1 precursor) of styrene and 4-amino styrene. The copolymerization ratio of the obtained P1 precursor was styrene/4-amino styrene=70/30 (on a molar basis).
[Preparation of P2 Precursor]

P2 precursor having a copolymerization ratio of styrene/4-amino styrene of 80/20 (on a molar basis) was obtained in the same manner as in [Preparation of P1 precursor] except that the blending ratio of monomer was changed.
[Preparation of P3 Precursor]

P3 precursor having a copolymerization ratio of styrene/4-amino styrene of 90/10 (on a molar basis) was obtained in the same manner as in [Preparation of P1 precursor] except that the blending ratio of monomer was changed.
[Preparation of P4 Precursor]

P4 precursor having a copolymerization ratio of styrene/4-amino styrene/normal butyl styrene of 60/30/10 (on a molar basis) was obtained in the same manner as in [Preparation of P1 precursor] except that normal butyl styrene was also used as the monomer.
[Preparation of P5 Precursor]

P5 precursor having a copolymerization ratio of styrene/4-(aminomethyl) styrene of 70/30 (on a molar basis) was obtained in the same manner as in [Preparation of P1 precursor] except that 4-(aminomethyl)styrene was used instead of amino styrene.
<Preparation of Resin (A)>
[Preparation of Resin P1]
(First Step)

The P1 precursor (72.8 g) and oxonorbornene acid anhydride represented by the following formula (41 g) were dissolved in tetrahydrofuran (THF) (300 g), and the obtained product was stirred under a nitrogen atmosphere for four hours. Subsequently, carbonyl diimidazole (61 g) was added thereto. The obtained product was stirred for six hours, and dropped into heptane (1.5 kg) to reprecipitate to obtain the protected resin 1 (a compound having a group represented by the formula (3)). The composition ratio of the obtained protected resin was calculated from $^{13}$C NMR. The calculated composition ratio was shown in the following structural formula. The number at the lower right of the parentheses in each constituent unit in the following structural formula represents the content (% by mole) of the constituent unit in each protected resin. Furthermore, from $^{13}$C NMR, the following structure was verified. The $^{13}$C NMR measurement result of the protected resin 1 is shown in FIG. 1. Note here that a measurement solvent of $^{13}$C NMR was acetone-d6.

[Chem. 12]

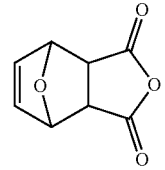

[Chem. 13]

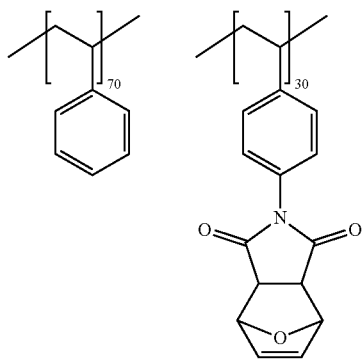

Protected Resin 1

-continued

Protected Resin 2

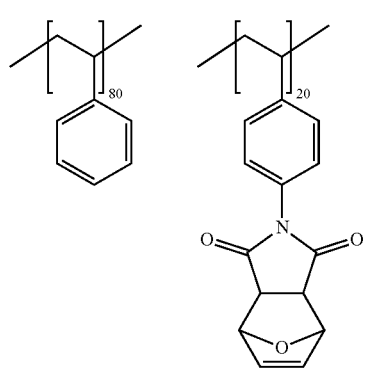

Protected Resin 3

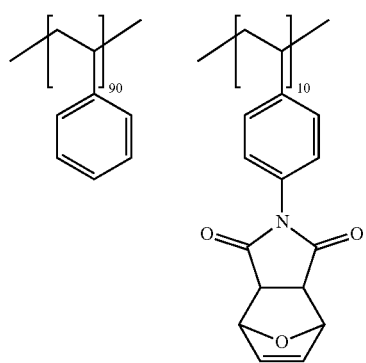

Protected Resin 4

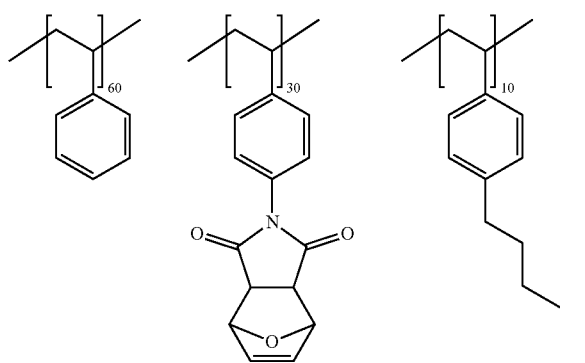

Protected Resin 5

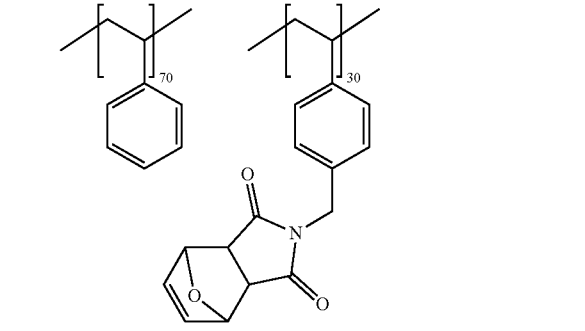

(Second Step)

Figure 2:
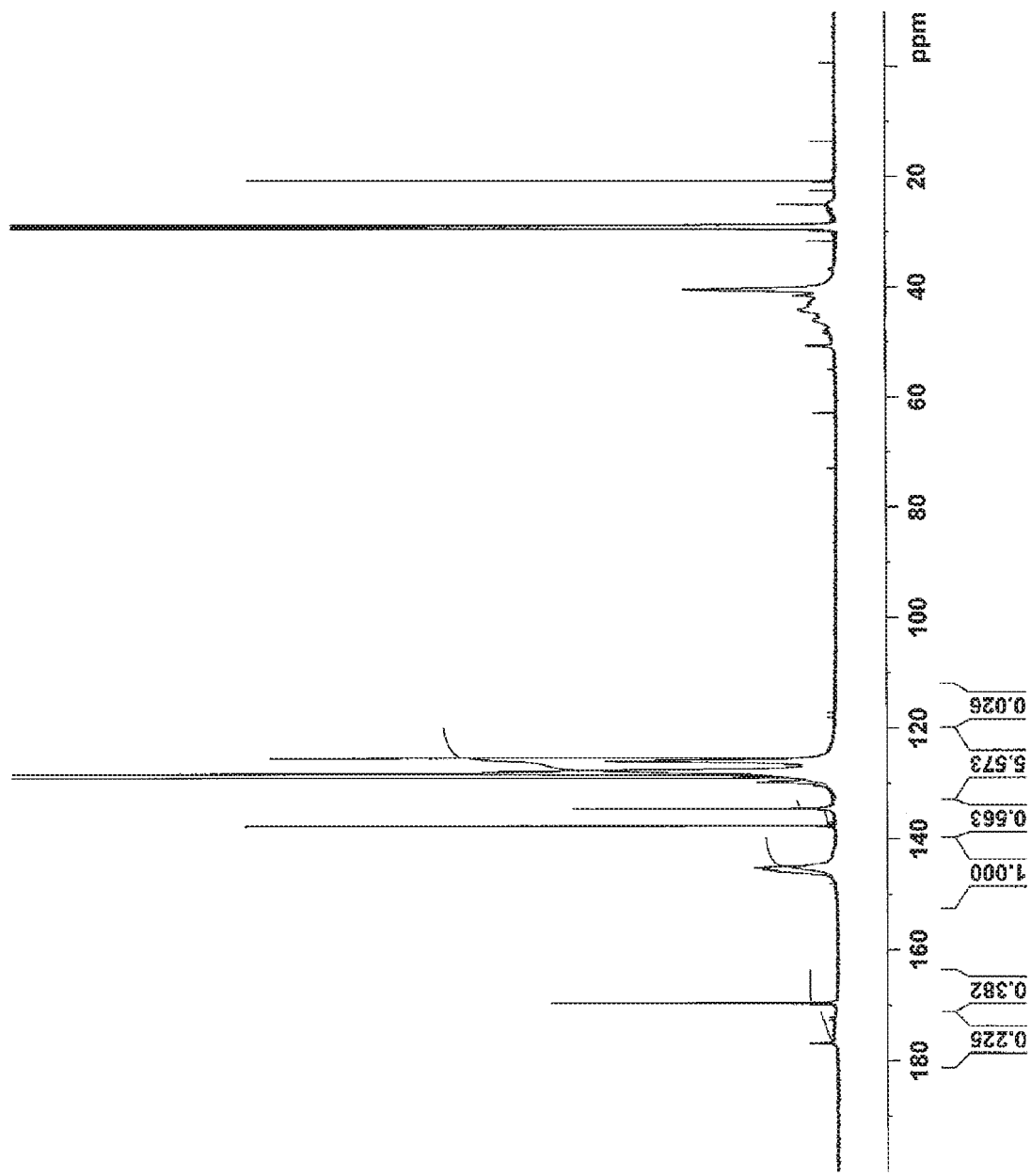
FIG. 2 is a view showing $^{13}$C NMR measurement result of a resin P1.

The obtained protected resin 1 was made into 20% by mass toluene solution. The solution was stirred while being refluxed for four hours, and then allowed to reprecipitate with heptane to obtain a solid resin P1 (17.8 g). The composition ratio of the obtained resin was calculated from $^{13}$C NMR. The calculated composition ratio is shown in the following structural formula. The number at the lower right of the parentheses in each constituent unit in the following structural formula represents the content (% by mole) of the constituent unit in each resin. Furthermore, in $^{13}$C NMR, a maleimide structure was confirmed from peak of carbonyl and peak of a double bond. The $^{13}$C NMR measurement result of the resin P1 is shown in FIG. 2. Note here that a measurement solvent of $^{13}$C NMR was acetone-d6. Furthermore, the mass average molecular weight (Mw) of the obtained resin was obtained by polystyrene conversion of gel permeation chromatography (GPC). The mass average molecular weight (Mw) of the resin P1 was 15000.

[Chem. 14]

Resin P1

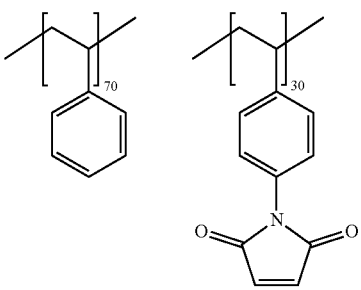

Resin P2

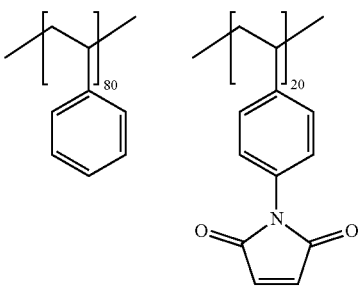

Resin P3

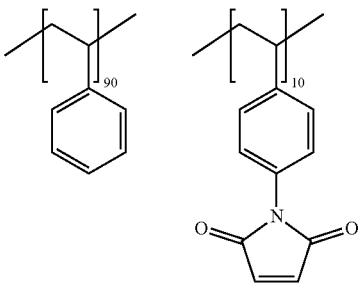

Resin P4

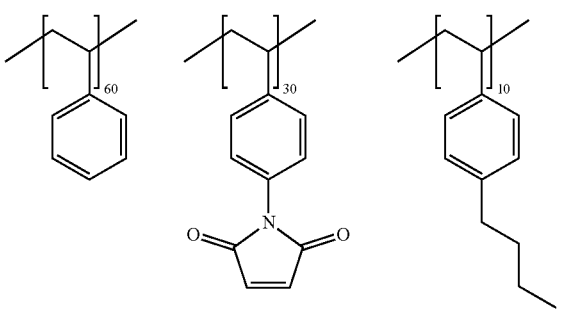

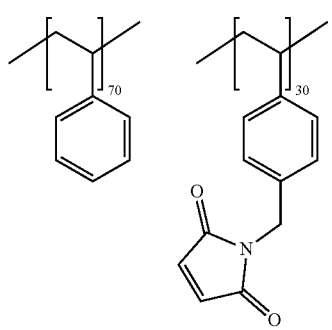

Resin P5

[Preparation of resins P2 to P5]

Protected resins 2 to 5 were respectively obtained in the first step, and solid resins P2 to P5 were respectively obtained in the second step, in the same manner as in [preparation of resin P1] except that precursors P2 to P5 were respectively used instead of the P1 precursor. The mass average molecular weight (Mw) of each of obtained resins P2 to P5 was 15000.

[Preparation 1 of Resin by Dehydration Ring Closure]

P1 precursor (20.0 g) and maleic anhydride (6.7 g) were dissolved in N-methyl-pyrrolidone (NMP) (100 g), and toluene (10 g) and methanesulfonic acid (1 g) were added thereto. Then, when the obtained product was stirred for four hours while heating at 150° C., gelation occurred and a large amount of insoluble matter is generated in a reaction solution. As a result, a solid resin was not able to be obtained.

[Preparation 2 of Resin by Dehydration Ring Closure]

When P1 precursor (20.0 g) and maleic anhydride (6.7 g) were dissolved in acetic anhydride (100 g), and the obtained product was stirred for four hours while being refluxed, gelation occurred and. As a result, a solid resin was not able to be obtained.

[Preparation of Resin by Ring Closure Using Carbonyldiimidazole]

P1 precursor (20.0 g) and maleic anhydride (6.7 g) were dissolved in THF (100 g), and carbonyldiimidazole (10 g) was added thereto. The obtained product was stirred for four hours at room temperature. The obtained reaction solution was allowed to reprecipitate with methanol-water mixed solution (methanol/water=1/1 (on a mass basis)) to obtain white solid (18 g). When the obtained white solid was subjected to $^{13}$C NMR measurement, the double bond peak disappeared, and the polymer was presumed to be a polymer in which imidazole had added to maleimide of the resin P1.

What is claimed is:

1. A method for producing a maleimide compound having a group represented by the following formula (a1):

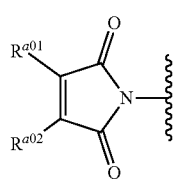

(a1)

wherein $R^{a01}$ and $R^{a02}$ are each independently a hydrogen atom, an alkyl group having 1 or more and 6 or less carbon atoms, a cycloalkyl group having 3 or more and 8 or less carbon atoms, or an aryl group having 6 or more and 12 or less carbon atoms, wherein the method comprises:

condensing a primary amino group in a raw material compound having the primary amino group and dicarboxylic anhydride represented by the following formula (a2):

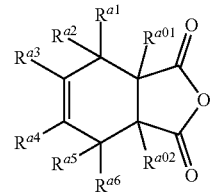

(a2)

wherein, in the formula (a2), $R^{a01}$ and $R^{a02}$ are the same as $R^{a01}$ and $R^{a02}$ in the formula (a1), $R^{a1}$ to $R^{a6}$ are each independently a hydrogen atom, a halogen atom, an alkyl group having 1 or more and 4 or less carbon atoms, or an alkoxy group having 1 or more and 4 or less carbon atoms, $R^{a1}$ and $R^{a5}$ may be bonded to each other to form —O—, —S—, —CH$_2$—, or —CR$^{a7}$R$^{a8}$—, and $R^{a3}$ and $R^{a4}$ may be bonded to each other to form a ring having 6 or more and 12 or less carbon atoms, $R^{a7}$ to $R^{a8}$ are each independently a hydrogen atom, an alkyl group having 1 or more and 4 or less carbon atoms, or an alkoxy group having 1 or more and 4 or less carbon atoms, to generate a group represented by the following formula (a3):

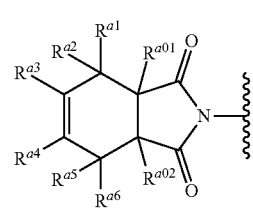

(a3)

wherein, in the formula (a3), $R^{a01}$ and $R^{a02}$ are the same as $R^{a01}$ and $R^{a02}$ in the formula (a1), and $R^{a1}$ to $R^{a6}$ are the same as $R^{a1}$ to $R^{a6}$ in the formula (a2; and heating a compound having the group represented by the formula (a3) generated by the condensing, and converting the group represented by the formula (a3) into a group represented by the formula (a1), wherein the raw material compound is a resin.

2. The method for producing the maleimide compound according to claim 1, wherein the resin is a polymer of a monomer having an unsaturated double bond.

3. The method for producing the maleimide compound according to claim 1, wherein the resin is a (meth)acrylic resin having a primary amino group at a terminal of a side chain, or a polystyrene resin having a primary amino group at a terminal of a side chain.

4. The method for producing the maleimide compound according to claim 1, comprising producing the raw material compound being the resin by homopolymerizing a monomer having the primary amino group or copolymerizing a monomer having the primary amino group and a comonomer.

5. The method for producing the maleimide compound according to claim 1, wherein the $R^{a01}$ and the $R^{a02}$ are each a hydrogen atom.

6. The method for producing the maleimide compound according to claim 5, wherein a compound represented by the formula (a2) is a compound represented by the following formula (a2-1):

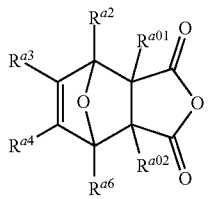

(a2-1)

wherein, in the formula (a2-1), $R^{a01}$, $R^{a02}$, $R^{a2}$, $R^{a3}$, $R^{a4}$, and $R^{a6}$ are the same as $R^{a01}$, $R^{a02}$, $R^{a2}$, $R^{a3}$, $R^{a4}$, and $R^{a6}$ in the formula (a2).

7. The method for producing the maleimide compound according to claim 1, wherein when the group represented by the formula (a3) is generated by the condensing, a condensation reaction is performed using carbonyldiimidazole.

8. A method for producing a maleimide compound having a group represented by the following formula (a1):

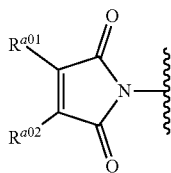

(a1)

wherein $R^{a01}$ and $R^{a02}$ are each independently a hydrogen atom, an alkyl group having 1 or more and 6 or less carbon atoms, a cycloalkyl group having 3 or more and 8 or less carbon atoms, or an aryl group having 6 or more and 12 or less carbon atoms,
wherein the method comprises:
condensing a primary amino group in a raw material compound having the primary amino group and dicarboxylic anhydride represented by the following formula (a2):

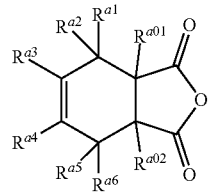

(a2)

wherein, in the formula (a2), $R^{a01}$ and $R^{a02}$ are the same as $R^{a01}$ and $R^{a02}$ in the formula (a1),
$R^{a1}$ to $R^{a6}$ are each independently a hydrogen atom, a halogen atom, an alkyl group having 1 or more and 4 or less carbon atoms, or an alkoxy group having 1 or more and 4 or less carbon atoms,
$R^{a1}$ and $R^{a5}$ may be bonded to each other to form —O—, —S—, —CH$_2$—, or —CR$^{a7}$R$^{a8}$—, and $R^{a3}$ and $R^{a4}$ may be bonded to each other to form a ring having 6 or more and 12 or less carbon atoms,
$R^{a7}$ to $R^{a8}$ are each independently a hydrogen atom, an alkyl group having 1 or more and 4 or less carbon atoms, or an alkoxy group having 1 or more and 4 or less carbon atoms,
to generate a group represented by the following formula (a3):

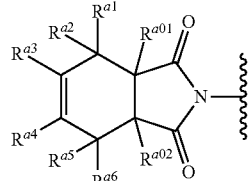

(a3)

wherein, in the formula (a3), $R^{a01}$ and $R^{a02}$ are the same as $R^{a01}$ and $R^{a02}$ in the formula (a1), and $R^{a1}$ to $R^{a6}$ are the same as $R^{a1}$ to $R^{a6}$ in the formula (a2), and
heating a compound having the group represented by the formula (a3) generated by the condensing, and converting the group represented by the formula (a3) into a group represented by the formula (a1),
wherein when the group represented by the formula (a3) is generated the condensing, a condensation reaction is performed using carbonyldiimidazole.

* * * * *